United States Patent [19]

Arndt et al.

[11] Patent Number: 4,605,767

[45] Date of Patent: Aug. 12, 1986

[54] PROCESS FOR THE PREPARATION OF 2,6-DICHLORO-4-NITROANILINE

[75] Inventors: Otto Arndt, Hofheim am Taunus; Theodor Papenfuhs, Frankfurt am Main, both of Fed. Rep. of Germany

[73] Assignee: Hoechst Aktiengesellschaft, Frankfurt am Main, Fed. Rep. of Germany

[21] Appl. No.: 734,972

[22] Filed: May 16, 1985

[30] Foreign Application Priority Data

May 18, 1984 [DE] Fed. Rep. of Germany ....... 3418495

[51] Int. Cl.$^4$ ...................... C07C 85/24; C07C 87/60
[52] U.S. Cl. ..................... 564/412; 564/441
[58] Field of Search .......................... 564/412

[56] References Cited

U.S. PATENT DOCUMENTS

| | | | |
|---|---|---|---|
| 2,733,269 | 1/1956 | Raimond et al. | 564/412 |
| 4,414,415 | 11/1983 | Aubouy et al. | 564/412 |

FOREIGN PATENT DOCUMENTS

| | | |
|---|---|---|
| 507950 | 12/1954 | Canada .................. 564/412 |
| 109189 | 7/1898 | Fed. Rep. of Germany . |
| 2648054 | 1/1982 | Fed. Rep. of Germany . |
| 160111 | 5/1983 | German Democratic Rep. . |
| 2077261 | 12/1981 | United Kingdom . |
| 836590 | 6/1981 | U.S.S.R. . |

OTHER PUBLICATIONS

Abstract of German Patent No. 2,648,054, dated 4/27/78.
Seyewetz et al, *Bulletin Soc. Chim. France*, 41: 197,203.
Körner, *Jahresber. Fortschritte Chem.*, 1875, p. 323.
Beilstein *Handbuch*, 12, p. 735, Syst. No. 1671, (1929).
Flürscheim, *J. Chem. Soc.*, 93: 1773-74 (1908).
Hall, *J. Amer. Chem. Soc.*, 52: 5115 and 5122 (1930).
Pausacker et al, *Austral. J. Chem.*, 12: 430 (1959).

*Primary Examiner*—Robert V. Hines
*Attorney, Agent, or Firm*—Connolly and Hutz

[57] ABSTRACT

Process for the preparation of 2,6-dichloro-4-nitroaniline by chlorination of 4-nitroaniline with chlorine bleaching liquor in water using acids, which comprises chlorinating 1 mole of 4-nitroaniline in 3-6 moles of hydrochloric acid (HCl) or nitric acid (HNO$_3$) in the form of a dilute, aqueous acid in the presence of a dispersing agent which is stable under the reaction conditions, the chlorination initially being carried out at 5° to 10° C. and then at 15°-20° C. and, finally, after 90-95% of the 2-chloro-4-nitroaniline intermediately formed has been converted into 2,6-dichloro-4-nitroaniline, the temperature of the aqueous suspension being increased from 15°-20° C. to 70° C., without further addition of chlorine bleaching liquor, and then by post-chlorinating, by renewed addition of chlorine bleaching liquor, at temperatures between 20° and 70° C., bringing the pH of the aqueous suspension to 9.0 and filtering off the 2,6-dichloro-4-nitroaniline formed and washing it with dilute mineral acid.

8 Claims, No Drawings

PROCESS FOR THE PREPARATION OF 2,6-DICHLORO-4-NITROANILINE

The invention relates to an improved process for the preparation, which is known per se, of 2,6-dichloro-4-nitroaniline from 4-nitroaniline by chlorination with hypochlorous acid (HClO) in water.

A process for the preparation of dichloronitroanilines, for example 2,6-dichloro-4-nitroaniline, in which 4-nitroaniline is reacted with hypochlorites in the presence of strong acids is described in German Pat. No. 2,648,054. According to the statements therein, the strong acid can be employed here in a wide concentration range of from 5 to 400% by weight (anhydrous acid), based on the weight of water added. The melting points given in the embodiment examples of the above patent for the 2,6-dichloro-4-nitroaniline obtained show that products of lesser quality are obtained by the process used. Thus, the melting points given in the patent vary between 174° and 182° C., whilst the highest melting point given in the literature is 195° C. (Atti della Reale Academia dei Lincei (Rendiconti) (5) 22 I, 826)).

A large excess of a mixture of 30% strength hydrochloric acid (25 moles) and 96% strength sulfuric acid (14 moles) is also used according to the statements in Russian Pat. No. 863,590, but the temperature is somewhat lower. (The melting point of the 2,6-dichloro-4-nitroaniline obtained here is 190.5°–191.5° C.). The disadvantage of this process is the high pollution of the effluent with hydrochloric and sulfuric acid.

The preparation of the product in question at relatively high temperatures (95°–110° C.) by chlorination of 4-nitroaniline by means of elemental chlorine in 15-25% strength hydrochloric acid is described in British Pat. No. 2,077,261. The product obtainable by this process is of poor quality (about 82 to at most 90% pure). The crude yields fall to below 75% if the hydrochloric acid concentrations used are less than 14%.

There are also references in the literature according to which extremely little hydrochloric acid is employed in the chlorination of 4-nitroaniline with sodium hypochlorite, namely only the amount necessary for neutralization of the sodium hydroxide (NaOH) liberated in the chlorination with sodium hypochlorite (NaOCl) (Bulletin de la Société Chimique des France (4), 41, 197, 203). A poor product quality is also to be expected here, since the authors of the literature reference in question refer to a literature reference according to which products of poor quality are to be expected under these conditions (Körner, Jahresberichte über die Fortschritte der Chemie [Yearly reports on the advances of chemistry] 1875, page 323, cf. Beilstein, 12, 735, Syst. No. 1671). It can be seen also from J. Chem. Soc. 93, page 1773 (1908) that impure 2,6-dichloro-5-nitroaniline is always formed in the chlorination of 4-nitroaniline with sodium hypochlorite in very dilute aqueous hydrochloric acid (for example less than 1% strength).

The resins which are thereby formed are probably to be attributed to the formation of nitrogen-chlorine compounds, such as, for example, N,N'-tetrachloro-4-nitroaniline. Other processes use organic additives, sometimes as catalysts (East German Pat. No. 160,111), and sometimes as diluents, or organic acid (East German Pat. No. 160,111; J. Chem. Soc. 93, 1774; and Austral. J. Chem. 12 (1959), 430).

All of these known processes have considerable disadvantages both from the ecological and economic viewpoint and in respect of the quality of the end product. The ecological deficiencies are to be seen as the high pollution of the effluent by inorganic and organic acids, and in some cases also by nitroaromatics (with poor yields). The economic deficiencies are the technical effort to be expended in regeneration of the organic additives and the working up of the effluent which may be necessary. The quality of the 2,6-dichloro-4-nitroaniline which can be obtained by these known processes can be seen from the purity contents and/or melting points given for these.

It has now been found that 2,6-dichloro-4-nitroaniline can be prepared in a high purity (purity of at least 96%) and a high yield (90% of theory) without the deficiencies mentioned, such as pollution of the effluent and technical effort for regeneration and working up of the effluent, by chlorination of 4-nitroaniline in water with chlorine bleaching liquor, by chlorinating 1 mole of 4-nitroaniline in 3-6 moles of hydrochloric acid (HCl) or nitric acid (HNO₃) in the form of a dilute, aqueous acid in the presence of a dispersing agent which is stable under the reaction conditions, the chlorination initially being carried out at 5°–10° C. and then at 15–20° C. and, finally, after 90–95% of the 2-chloro-4-nitroaniline intermediately formed has been converted into 2,6-dichloro-4-nitroaniline, the temperature of the aqueous suspension being increased from 15°–20° C. to 70° C., without further addition of chlorine bleaching liquor and preferably with renewed addition of dispersing agent, and then by afterchlorinating, by renewed addition of chlorine bleaching liquor, at temperatures between 20° and 70° C., subsequently bringing the pH of the aqueous suspension to 9.0 and filtering off the 2,6-dichloro-4-nitroaniline formed and washing it with dilute mineral acid.

Hydrochloric acid (30–31% strength) is preferably used for the chlorination of the 4-nitroaniline in the process. However, it is also possible and particularly economical also to use the washing acid obtained in the present process (in the context of recycling) by adding it to the acid taken.

If hydrochloric acid is used, the minimum amount of acid to be employed is determined 1) by the requirement of 1 equivalent of hydrochloric acid (HCl) to form the 4-nitroaniline hydrochloride (Am. Soc. 52 (1930) 5115 and 5122) and of 2 equivalents of hydrochloric acid for the chlorination of 4-nitroaniline with sodium hypochlorite in accordance with the general equation

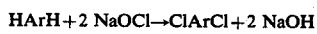

$$HArH + 2\ NaOCl \rightarrow ClArCl + 2\ NaOH$$

corresponding to a total of 3 equivalents (=3 moles) of HCl per mole of 4-nitroaniline, and 2) by the requirement that contact between 4-nitroaniline or 2-chloro-4-nitroaniline and hypochlorous acid (HOCl) above pH 0.5 must be avoided, for which, in addition to the 3 equivalents according to (1), 1-3 equivalents of hydrochloric acid (HCl) are sufficient according to the invention.

If, for example, only 2 equivalents of HCl are employed, which are just sufficient to neutralize the two equivalents of NaOH liberated when 1 mole of 4-nitroaniline is reacted with 2 moles of NaOCl in accordance with the above equation, a product with a particularly poor quality and yield is obtained. In particular, it has also been found that falling below an HCl concentration of 14%, which is described as a disadvantage in British Pat. No. 2,077,261, is of no consequence for the process conditions according to the invention.

By the after-treatment of the suspension at 70° C. (without further addition of chlorine bleaching liquor), about 6% of 2-chloro-4-nitroaniline which was enveloped by undissolved solid particles of 2,6-dichloro-4-nitroaniline is liberated.

In the case of chlorination in a hydrochloric acid medium, it is advantageous to carry out the reaction in an aqueous medium, the HCl concentration of which is about 5 to about 14% by weight.

Since the processes of considerably different design which are described in the literature give only unsatisfactory results (see above), it must be considered to be surprising that the chlorination according to the invention is effected with NaOCl by using a minimum amount of 3 and a maximum amount of 6 moles of hydrochloric acid or nitric acid, and in addition a dispersing agent, and by carrying out after-treatment with heat with postchlorination. In contrast to the claim made in Bulletin de la Soc. Chim. de France loc. cit., that no side reactions proceed apart from the nuclear chlorination, according to our investigations, by-products are certainly formed, and even traces of these adversely influence the quality of the end product because of their color intensity. Their removal during filtration of the suspension, rendered alkaline, in the course of the process according to the invention is a clear advance.

A requirement of the dispersing agent to be employed is that it is relatively stable under the conditions of the chlorination according to the process. Examples of suitable dispersing agents are compounds of the group comprising alkanesulfonates (in particular secondary alkanesulfonates), aralkylsulfonates (alkyl-benzenesulfonates and alkylnaphthalenesulfonates), primary alkyl-sulfates (fatty alcohol sulfates, fatty alkyl-sulfates and fatty alcohol sulfonates), secondary alkyl-sulfates, fatty acid condensation products (condensates with substances containing amino groups, condensates with substances containing hydroxyl groups, and condensates with aromatic hydrocarbons), polyglycol ethers and pyridine bases. In respect of the amount to be employed, it is advantageous to use about 5–45 parts by weight of dispersing agent per mole of 4-nitroaniline.

Further details and preferred embodiments of the process according to the invention will be described below:

To prepare for the chlorination, the 4-nitroaniline is stirred in 5–10 times the amount of water, with the addition of a suitable dispersing agent, for example a secondary alkanesulfonate. If hydrochloric acid is used, at least 3 equivalents (3 moles) of 31% strength hydrochloric acid, preferably 5–6 equivalents (5–6 moles), per mole of 4-nitroaniline, are then allowed to run into the suspension. It is not necessary to add more than 6 equivalents (6 moles) of HCl; this would only lead to an increased pollution of the effluent and increased emission of chlorine. The use of 5–6 equivalents (moles) of HCl at a concentration of about 13%, based on the total aqueous solution, is therefore preferred because the 4-nitroaniline then dissolves. Recycling acids can also be employed, for example the mineral acid, for example hydrochloric acid, employed for washing the 2,6-dichloro-4-nitroaniline.

Chlorine bleaching liquor in the process according to the invention is understood as meaning aqueous solutions of NaOCl and NaCl, which can be prepared by passing chlorine into cold aqueous sodium hydroxide solution (a 13.5% strength by weight chlorine bleaching liquor contains 166 g of active chlorine per 1,229 g=1 liter, corresponding to 2.34 moles of NaOCl per liter) (Gmelins Handbuch der anorganischen Chemie [Gmelins handbook of inorganic chemistry] 6 (1927), page 293; and Ullmanns Encyklopädie der technischen Chemie [Ullmanns encyclopedia of industrial chemistry] 9, 4th edition (1975), page 544).

Before the chlorination, the suspension of the 4-nitroaniline or the solution of its hydrochloride in the amount of hydrochloric acid or nitric acid employed according to the invention is cooled to 5°–10° C.

The chlorination proceeds in two stages:
(1) formation of 2-chloro-4-nitroaniline;
(2) formation of 2,6-dichloro-4-nitroaniline.

Both stages require somewhat different conditions in respect of temperature and duration. The preferred temperatures for the first stage are 5°–10° C., and those for the second stage are initially 15°–20° C. and then 70° C. The second stage is considerably more critical than the first stage in respect of completeness of the conversion. 2–3 hours are required for the first stage, chiefly because of the increased cooling requirement. The second stage requires the after-treatment with heat according to the invention, starting from 15°–20° C., at 70° C. in the presence of the dispersing agent, which is preferably added again, with subsequent post-chlorination at 20° or 70° C. Longer times for the second stage than 5–7 hours at initially 15° to 20° C. and 2 hours at the upper temperature of 70° C. are uneconomical because of the reduction in the space/time yield thereby caused. Shorter times than 1 hour in the second stage lead to incomplete conversion.

If the optimum conditions according to the invention are maintained, complete conversion of the 4-nitroaniline to 2,6-dichloro-4-nitroaniline is already achieved with amounts of sodium hypochlorite of only a little more than 2 equivalents (for example 228 mol %). If the conditions are adverse, even substantially larger excesses of chlorine bleaching liquor may be useless. After checking the end point of the conversion by thin layer chromatography, any residual active chlorine still present is destroyed with an equivalent amount of 40% strength sodium bisulfite liquor. The light yellow suspension is filtered at 70° C. It is advisable here to include the possibility of removing traces of highly coloring secondary components. For this, the suspension is also brought to pH 9.0 with 33% strength aqueous sodium hydroxide solution before the filtration. At this point, further 40% strength sodium bisulfite liquor can be added for safety. Dark brown mother liquors are obtained on filtration, whilst a light-colored product is filtered off. Hot washing is then carried out with water, if appropriate with further addition of dispersing agent, and then with, for example, 2% strength hydrochloric acid and finally with water again. The filtration operations can be carried out on an open suction filter. There is no pollution by chlorine.

The 2,6-dichloro-4-nitroaniline is obtained in a yield of 90% of theory and with a purity of at least 97% (according to high pressure liquid chromatography ("HPLC")) and a melting point of 187°–191° C. (according to data in the literature, the melting point is 192° C. at a purity of 99.6%). 2-Chloro-4-nitroaniline (2.1%) is contained as an impurity (HPLC). The chlorination can of course also be stopped at the 1st stage, 2-chloro-4-nitroaniline being obtained (cf. German Reich Pat. No. 109,189 (1898)).

Comparison with the abovementioned processes known from the literature clearly shows the advances given by the process according to the invention in respect of simplicity of the procedure and improvement in quality. 2,6-Dichloro-4-nitroaniline is an important intermediate for the preparation of 3,5-dichloroaniline, which is an intermediate for plant protection active ingredients. It is also an intermediate for the preparation of azo dyestuffs.

The following examples serve to illustrate the process according to the invention, without limiting it thereto. Parts denote parts by weight. The parts by weight of the dispersing agent are understood as standardized 60% strength aqueous solutions.

EXAMPLE 1

(Effect of the amount of hydrochloric acid present)

140 parts (1 mole) of 4-nitroaniline in commercially available technical grade moist or technical grade dry form (melting point 147° C.) are introduced, at about 25° C. under customary stirring conditions, into 1000 parts of water, to which 5 parts of a dispersing agent (secondary alkanesulfonate) are added. The mixture is then cooled to 5°–10° C. 706 parts of 31% strength hydrochloric acid (6 moles) are allowed to run in. 565 parts of 13.5% strength chlorine bleaching liquor (corresponding to 1.07 moles of NaOCl=1.07 moles of active chlorine) are added dropwise to the solution at 5°–10° C. in the course of 3 hours, with stirring and further external cooling. The 2-chloro-4-nitroaniline crystallizes out. A sample filtered off contains only about 1–2% of 4-nitroaniline. After 5 parts of dispersing agent have been added again, if appropriate, the temperature of the suspension is allowed to rise to 15°–20° C. 565 parts of 13.5% strength chlorine bleaching liquor (corresponding to 1.07 moles of NaOCl=1.07 moles of active chlorine) are then again added dropwise at 15°–20° C. in the course of 5 hours, with stirring.

After the end of the conversion has been checked by thin layer chromatography, residual active chlorine still present is destroyed with an equivalent amount of 40% strength aqueous sodium bisulfite solution, 15 parts as a rule being adequate. The mixture is then warmed to 60°–65° C. in the course of about 30 minutes. The thin, yellow, fine-particled suspension is brought from pH 0 to pH 9.0 with 476 parts of 33% strength sodium hydroxide solution. The now thin, light brown suspension is filtered off with suction over a filter at 70° C., after further addition of 15 parts of 40% strength sodium bisulfite solution. The mother liquor is dark brown. The product is then washed successively with (1) 1000 parts of water of 70°–75° C., to which 2.5 parts of dispersing agent are added,
(2) 2000 parts of 0.2% strength hydrochloric acid at 70°–75° C. and
(3) 1000 parts of water of 70°–75° C.

After drying at 60° C., 191 parts of dry product with a purity of 94.0% of 2,6-dichloro-4-nitroaniline (HPLC) and a melting point of 183°–187° C., corresponding to a yield of 86% of theory, are obtained as a yellow powder, which, when dissolved in dimethylformamide (100 mg/10 ml of dimethylformamide) gives a solution light brownish-yellow in color. The content of 2-chloro-4-nitroaniline is 5.5%. The effluent (about 6900–7000 parts, pH 1.2) contains about 16 parts of nitroaromatics and, after appropriate pretreatment, can be passed to biological purification.

EXAMPLE 2

(Effect of the amount of hydrochloric acid present)

The procedure is as described in Example 1, but with the difference that only 353 parts of 31% strength hydrochloric acid (3 moles) are taken. The 4-nitroaniline now no longer dissolves. Nevertheless, after drying, almost the same amount by weight of dry product (193 parts) is obtained as in accordance with Example 1, but with a lower purity of about 82% of 2,6-dichloro-4-nitroaniline, a content of 9% of 2-chloro-4-nitroaniline and a melting point of 176°–80° C., corresponding to a yield of 76% of theory, as a light brown powder, which, when dissolved in dimethylformamide (100 mg/10 ml of dimethylformamide) gives a solution which is brown in color.

The chlorine emission at the end of the chlorination is lower in the procedure according to Example 2 than in that according to Example 1.

EXAMPLE 3

(Effect of the amount of hydrochloric acid present)

The procedure followed is as described in Example 1, but with the difference that only 235 parts of 31% strength hydrochloric acid (2 moles) are taken. A decidedly poor yield is obtained, namely only 168 parts of dry product with a purity of 47% of 2,6-dichloro-4-nitroaniline (corresponding to a yield of 38% of theory) and a content of 11% of 2-chloro-4-nitroaniline, with a melting point of 150°–165° C. The result is also considerably poorer than the result of Example 2.

It is seen that the actual drop in quality and yield occurs if less than 3 moles of hydrochloric acid are taken.

EXAMPLE 4

(Adverse effect of the use of too large an amount of chlorine bleaching liquor in the course of the second reaction stage)

The procedure followed is as described in Example 1, but with the difference that only 588 parts of 31% strength hydrochloric acid (5 moles) are taken and the 2nd portion of chlorine bleaching liquor added is 635 parts.

187 parts of dry product with a purity of 91% of 2,6-dichloro-4-nitroaniline (corresponding to a yield of 82% of theory) and a content of 5% of 2-chloro-4-nitroaniline, with a melting point of 182°–186° C., but with a darker color of the solution than in the procedure according to Example 1.

EXAMPLE 5

(Addition of washing acid to the acid taken)

The procedure is as described in Example 4, but with the difference that washing acid (hydrochloric acid) is employed in addition to the hydrochloric acid taken, so that a total of about 5.3 moles of HCl are taken. After recycling twice, 179 parts of dry product with a purity of 96% of 2,6-dichloro-4-nitroaniline (corresponding to a yield of 83% of theory) and a content of 3% of 2-chloro-4-nitroaniline and with a melting point of 175°–183° C. are obtained.

EXAMPLE 6

(Effect of the absence of dispersing agent on the chlorination)

The procedure followed is as described in Example 4, but with the difference that no dispersing agent is added. 183 parts of dry product with a purity of only 88% of 2,6-dichloro-4-nitroaniline (corresponding to a yield of only 78% of theory) and a content of 6% of 2-chloro-4-nitroaniline and with a melting point of only 170°–182° C. are obtained. The color of the solution is somewhat darker than that in the procedure according to Example 4.

EXAMPLE 7

(This Example has all the features of the process according to the invention and is thus the optimum procedure)

The procedure followed is as described in Example 1, but with the difference that, after reaction of 1130 parts of chlorine bleaching liquor in the form described in Example 1, the mixture is then heated to 70° C. and a further 10 parts of dispersing agent (secondary alkanesulfonate) are added (a total thus of 22.5 parts of dispersing agent). The mixture is allowed to cool to 20° C. and another post-chlorination with 70 parts of chlorine bleaching liquor is carried out at 20° C. 193 parts of dry product with a purity of 96% of 2,6-dichloro-4-nitroaniline (corresponding to a yield of 90% of theory) and a content of 2.1% of 2-chloro-4-nitroaniline and with a melting point of 187°–191° C. are obtained. The solution is light brownish-yellow in color, as in the procedure according to Example 1.

EXAMPLE 8

(Adverse effect of the use of somewhat more chlorine bleaching liquor)

The procedure followed is as described in Example 7, but with the difference that 140 parts of chlorine bleaching liquor are employed in the post-chlorination. Only 179 parts of dry product of melting point 186°–189° C. are obtained.

EXAMPLE 9

(Adverse effect of the use of less dispersing agent)

The procedure followed is as described in Example 7, but with the difference that a total of only 10 parts and not 22.5 parts of dispersing agent are employed. 187 parts of dry product with a melting point of only 180°–185° C. are obtained.

EXAMPLE 10

(This example contains all the features of the process according to the invention)

The procedure followed is as described in Example 7, but with the difference that the post-chlorination is carried out at 70° C.

186 parts of dry product with a purity of 97.5% of 2,6-dichloro-4-nitroaniline (corresponding to a yield of 88% of theory) and a content of 0.8% of 2-chloro-4-nitroaniline and with a melting point of 187°–191° C. are obtained.

The solution is light orange in color and lighter than in the procedure according to Example 7.

EXAMPLE 11

(Limited adverse effect of the absence of dispersing agent when all the other process features according to the invention are present)

The procedure followed is as described in Example 10, but with the difference that no dispersing agent is used. 185 parts of dry product with a purity of 96% of 2,6-dichloro-4-nitroaniline (corresponding to a yield of 86% of theory) and a content of 1.4% of 2-chloro-4-nitroaniline and with a melting point of 183°–188° C. are obtained. The solution is light orange to brown in color, and is somewhat darker than in the procedure according to Example 10.

EXAMPLE 12

(Adverse effect of too rapid addition of the second portion of chlorine bleaching liquor in the absence of cooling on the yield)

The procedure followed is as described in Example 1, but with the difference that the second portion of 565 parts of 13.5% strength chlorine bleaching liquor is allowed to run in over a period of 15 minutes without further external cooling, whereupon the temperature rises to 25° C. The mixture is then subsequently stirred at 25° C. for 1 hour and the chlorination is brought to completion by the after-treatment with heat and post-chlorination at 70° C. described in Examples 7 and 10. 181 parts of dry product with a purity of 97% of 2,6-dichloro-4-nitroaniline (corresponding to a yield of 85% of theory) and a content of 1.2% of 2-chloro-4-nitroaniline and with a melting point of 186°–188° C. are obtained.

EXAMPLE 13

(Obtaining of exclusively the monochloro derivative of 4-nitroaniline when the reaction is interrupted after the 1st stage)

The procedure followed is as described in Example 1, but with the difference that only the 1st portion of chlorine bleaching liquor is added. The 2-chloro-4-nitroaniline formed is filtered off with suction at 10° C. and washed with 1000 parts of drinking water, 2000 parts of 5% strength sodium carbonate solution and again with 1000 parts of drinking water. 167 parts of 2-chloro-4-nitroaniline with a melting point of 94°–101° C. are obtained in a yield of more than 90% of theory.

We claim:

1. A process for the preparation of 2,6-dichloro-4-nitroaniline by chlorination of 4-nitroaniline with chlorine bleaching liquor in water using acids, which comprises chlorinating 1 mole of 4-nitroaniline in 3–6 moles of hydrochloric acid (HCl) or nitric acid ($HNO_3$) in the form of a dilute, aqueous acid in the presence of a dispersing agent which is stable under the reaction conditions, the chlorination initially being carried out at 5° to 10° C. and then at 15°–20° C. and, finally, after 90–95% of the 2-chloro-4-nitroaniline intermediately formed has been converted into 2,6-dichloro-4-nitroaniline, the temperature of the aqueous suspension being increased from 15°–20° C. to 70° C., without further addition of chlorine bleaching liquor, and then by post-chlorinating, by renewed addition of chlorine bleaching liquor, at temperatures between 20° and 70° C., bringing the pH of the aqueous suspension to 9.0 and filtering off the 2,6-dichloro-4-nitroaniline formed and washing it with dilute mineral acid.

2. The process as claimed in claim 1, wherein the chlorination is carried out in the presence of 3 to 6 moles of hydrochloric acid (HCl), based on the 4-nitroaniline employed.

3. The process as claimed in claim 1 wherein the chlorinating is carried out in an aqueous hydrochloric acid medium, in which the concentration of hydrochloric acid (HCl) is about 5 to about 14 per cent by weight.

4. The process as claimed in claim 1, wherein the after-treatment is carried out by heating the suspension without the addition of chlorine bleaching liquor and with renewed addition of a dispersing agent which is stable under the reaction conditions.

5. A process for the preparation of substantially pure 2,6-dichloro-4nitroaniline by chlorinatin of 4-nitroaniline with chloring bleaching liquor in water using acids, which comprises chlorinating 1 mole of 4-nitroaniline in 3-6 mole of hydrochloric acid (HCl) or nitric acid (HNO$_3$) in the form of a dilute, aqueous acid in the presence of a dispersing agent which is stable under the reaction conditions, the chlorination initially being carried out at 5° to 10° C. and then at 15°-20° C. and, finally, after 90-95% of the 2-chloro-4-nitroaniline intermediately formed has been converted into 2,6-dichloro-4-nitroaniline, the temperature of the aqueous suspension being increased from 15°-20° C. to 70° C., without further addition of chlorine bleaching liquor, and then by post-chlorinating, by renewed addition of chlorine bleaching liquor, at temperatures between 20° and 70° C., bringing the pH of the aqueous sispension to 9.0 and filtering off the 2,6-dichloro-4-nitroaniline formed and washing it with dilute mineral acid to provide 2,6-dichloro-4-nitroaniline of a purity of 96% or above, and a melting point of 187°-191° C. and in a yield of 80% or above.

6. The process as claimed in claim 5, wherein the chlorination is carried out in the presence of 3 to 6 moles of hydrochloric acid (HCl), based on the 4-nitroaniline employed.

7. The process as claimed in claim 5, wherein the chloringating is carried out in an aqueous hydrochloric acid medium, in which the concentration of hydrochloric acid (HCl) is about 5 to about 14 percent by weight.

8. The process as claimed in claim 5, wherein the after-treatment is carried out by heating the suspension without the addition of chlorine bleaching liquor and with renewed addition of a dispersing agent which is stable under the reaction conditions.

* * * * *

UNITED STATES PATENT AND TRADEMARK OFFICE
CERTIFICATE OF CORRECTION

PATENT NO. : 4,605,767
DATED : AUGUST 12, 1986
INVENTOR(S) : OTTO ARNDT, THEODOR PAPENFUHS

It is certified that error appears in the above-identified patent and that said Letters Patent is hereby corrected as shown below:

Claim 5, line 3, delete "chloring" and insert -- chlorine --.

Claim 7, line 2, delete "chloringating" and insert -- chlorinating --.

Signed and Sealed this

Second Day of December, 1986

Attest:

DONALD J. QUIGG

*Attesting Officer*  *Commissioner of Patents and Trademarks*